United States Patent
Bhagwat et al.

(10) Patent No.: US 9,789,097 B2
(45) Date of Patent: *Oct. 17, 2017

(54) PHARMACEUTICAL COMPOSITIONS COMPRISING ANTIBACTERIAL AGENTS

(71) Applicant: WOCKHARDT LIMITED, Aurangabad (IN)

(72) Inventors: Sachin Bhagwat, Aurangabad (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/030,310

(22) PCT Filed: Oct. 22, 2014

(86) PCT No.: PCT/IB2014/065521
§ 371 (c)(1),
(2) Date: Apr. 18, 2016

(87) PCT Pub. No.: WO2015/059642
PCT Pub. Date: Apr. 30, 2015

(65) Prior Publication Data
US 2016/0303094 A1    Oct. 20, 2016

(30) Foreign Application Priority Data

Oct. 22, 2013 (IN) .......................... 3308/MUM/2013

(51) Int. Cl.
| | |
|---|---|
| A61K 31/44 | (2006.01) |
| A61K 31/397 | (2006.01) |
| A61K 31/195 | (2006.01) |
| A61K 31/439 | (2006.01) |
| A61K 31/407 | (2006.01) |
| A61K 31/198 | (2006.01) |

(52) U.S. Cl.
CPC .......... *A61K 31/439* (2013.01); *A61K 31/198* (2013.01); *A61K 31/407* (2013.01)

(58) Field of Classification Search
CPC ... A61K 31/439; A61K 31/407; A61K 31/198
USPC .................................. 514/300, 210.09, 562
See application file for complete search history.

(56) References Cited

U.S. PATENT DOCUMENTS

| | | | |
|---|---|---|---|
| 8,969,334 B2 * | 3/2015 | Patil ..................... | C07D 471/08 514/203 |
| 9,090,616 B2 * | 7/2015 | Patil ..................... | C07D 471/08 |
| 2008/0090825 A1 * | 4/2008 | Chikauchi ............ | A61K 31/445 514/237.5 |

FOREIGN PATENT DOCUMENTS

WO    WO2013038330 A1    3/2013

OTHER PUBLICATIONS

Esterly et al., Predictability of doripenem susceptibility in Acinetobacter baumannii isolates based on other carbapenem susceptibilities and bla OXA gene status. Pharmacotherapy. Apr. 2010;30(4):354-360. doi: 10.1592/phco.30.4.354.
Castanheira et al., Antimicrobial activities of doripenem and other carbapenems against Pseudomonas aeruginosa, other nonfermentative bacilli, and Aeromonas spp. Diagn Microbiol Infect Dis. Apr. 2009;63(4):426-433.
Quinteros M G et al: "In Vitro Imipenem-Sulbactam Activity against Multidrug Resistant Acinetobacter calcoaceticus-baumannii complex (ABC) by Time-Kill Assay", Abstracts of the Interscience Conference on Antimicrobial Agents and Chemotherapy, vol. 1 • 52, 2812, p. E202, XP009181733, & 52nd Interscience Conference on Antimicrobial Agents and Chemotherapy (ICAAC); San Francisco, CA, USA; Sep. 9-12, 2012, I SSN: 0733-6373.

* cited by examiner

*Primary Examiner* — Shengjun Wang
(74) *Attorney, Agent, or Firm* — Bio Intellectual Property Services LLC (Bio IPS); O. (Sam) Zaghmout

(57) ABSTRACT

Pharmaceutical compositions comprising imipenem or a pharmaceutically acceptable derivative, and a compound of Formula (I) or a stereoisomer or a pharmaceutically acceptable derivative thereof are disclosed.

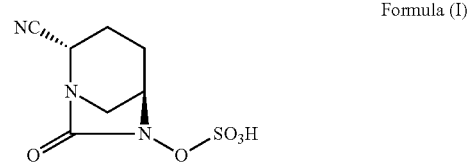

Formula (I)

23 Claims, No Drawings

PHARMACEUTICAL COMPOSITIONS COMPRISING ANTIBACTERIAL AGENTS

RELATED PATENT APPLICATIONS

This application claims priority to Indian Patent Application No. 3308/MUM/2013 filed on Oct. 22, 2013, the disclosures of which are incorporated herein by reference in its entirety as if fully rewritten herein.

FIELD OF THE INVENTION

The invention relates to antibacterial compositions and methods for treating or preventing bacterial infections.

BACKGROUND OF THE INVENTION

Bacterial infections continue to remain one of the major causes contributing towards human diseases. One of the key challenges in treatment of bacterial infections is the ability of bacteria to develop resistance to one or more antibacterial agents over time. Examples of such bacteria that have developed resistance to typical antibacterial agents include: Penicillin-resistant *Streptococcus pneumoniae*, Vancomycin-resistant *Enterococci*, and Methicillin-resistant *Staphylococcus aureus*. The problem of emerging drug-resistance in bacteria is often tackled by switching to newer antibacterial agents, which can be more expensive and sometimes more toxic. Additionally, this may not be a permanent solution as the bacteria often develop resistance to the newer antibacterial agents as well in due course. In general, bacteria are particularly efficient in developing resistance, because of their ability to multiply very rapidly and pass on the resistance genes as they replicate.

Treatment of infections caused by resistant bacteria remains a key challenge for the clinician community. One example of such challenging pathogen is *Acinetobacter baumannii* (*A. baumannii*), which continues to be an increasingly important and demanding species in healthcare settings. The multidrug resistant nature of this pathogen and its unpredictable susceptibility patterns make empirical and therapeutic decisions more difficult. *A. baumannii* is associated with infections such as pneumonia, bacteremia, wound infections, urinary tract infections and meningitis.

Therefore, there is a need for development of newer ways to treat infections that are becoming resistant to known therapies and methods. Surprisingly, it has been found that a compositions comprising imipenem and certain nitrogen containing bicyclic compounds (disclosed in PCT/IB2012/054706) exhibit unexpectedly synergistic antibacterial activity, even against highly resistant bacterial strains.

SUMMARY OF THE INVENTION

Accordingly, there are provided pharmaceutical compositions comprising: (a) imipenem or a pharmaceutically acceptable derivative thereof, and (b) a compound of Formula (I) or a stereoisomer or a pharmaceutically acceptable derivative thereof:

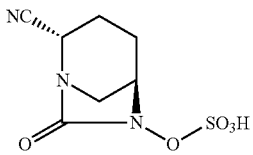

Formula (I)

In one general aspect, there are provided pharmaceutical compositions comprising: (a) imipenem or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is present in the composition in an amount from about 0.25 gram to about 4 gram per gram of imipenem or a pharmaceutically acceptable derivative thereof.

In yet another general aspect, there are provided methods for treating or preventing a bacterial infection in a subject, said methods comprising administering to said subject an effective amount of a pharmaceutical composition comprising: (a) imipenem or a pharmaceutically acceptable derivative thereof; and (b) a compound of Formula (I) or a stereoisomer or a pharmaceutically acceptable derivative thereof.

In another general aspect, there are provided methods for treating or preventing a bacterial infection in a subject, said methods comprising administering to said subject an effective amount of a pharmaceutical composition comprising: (a) imipenem or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is present in the composition in an amount from about 0.25 gram to about 4 gram per gram of imipenem or a pharmaceutically acceptable derivative thereof.

In yet another general aspect, there are provided methods for treating or preventing a bacterial infection in a subject, said methods comprising administering to said subject an effective amount of: (a) imipenem or a pharmaceutically acceptable derivative thereof; and (b) a compound of Formula (I) or a stereoisomer or a pharmaceutically acceptable derivative thereof.

In another general aspect, there are provided methods for treating or preventing a bacterial infection in a subject, said methods comprising administering to said subject an effective amount of: (a) imipenem or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is administered in an amount from about 0.25 gram to about 4 gram per gram of imipenem or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety as if fully rewritten herein.

The inventors have surprisingly discovered that a pharmaceutical composition comprising: (a) imipenem or a pharmaceutically acceptable derivative thereof, and (b) a compound of Formula (I) or a stereoisomer or a pharmaceutically acceptable derivative thereof exhibits unexpectedly improved antibacterial efficacy, even against highly resistant bacteria, including those producing extended spectrum beta-lactamase enzymes (ESBLs).

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of other floras, which are not desirable. The term "infection" includes infection caused by bacteria.

The term "treat", "treating" or "treatment" as used herein refers to administration of a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions, or one or more of pharmaceutically active ingredients discussed herein, with or without additional pharmaceutically active or inert ingredients, in order to: (i) reduce or eliminate either a bacterial infection, or one or more symptoms of a bacterial infection, or (ii) retard progression of a bacterial infection, or one or more symptoms of a bacterial infection, or (iii) reduce severity of a bacterial infection, or one or more symptoms of a bacterial infection, or (iv) suppress clinical manifestation of a bacterial infection, or (v) suppress manifestation of adverse symptoms of a bacterial infection.

The terms "pharmaceutically effective amount" or "therapeutically effective amount" or "effective amount" as used herein refer to an amount, which has a therapeutic effect or is the amount required to produce a therapeutic effect in a subject. For example, a "therapeutically effective amount" or "pharmaceutically effective amount" or "effective amount" of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). Such effective amount depends on several factors, including but not limited to, the microorganism (e.g. bacteria) involved, characteristics of the subject (for example height, weight, sex, age and medical history), severity of infection and particular type of the antibacterial agent used. For prophylactic treatments, a prophylactically effective amount is that amount which would be effective in preventing the bacterial infection.

The term "administration" or "administering" refers to and includes delivery of a composition, or one or more pharmaceutically active ingredients to a subject, including for example, by any appropriate method, which serves to deliver the composition or its active ingredients or other pharmaceutically active ingredients to the site of infection. The method of administration may vary depending on various factors, such as for example, the components of the pharmaceutical composition or type/nature of the pharmaceutically active or inert ingredients, site of the potential or actual infection, the microorganism involved, severity of the infection, age and physical condition of the subject and a like. Some non-limiting examples of ways to administer a composition or a pharmaceutically active ingredient to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop and mouthwash. In case of a pharmaceutical composition comprising more than one ingredients (active or inert), one of the ways of administering such composition is by admixing the ingredients (e.g. in the form of a suitable unit dosage form such as tablet, capsule, solution, powder or a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term "growth" also includes maintenance of on-going metabolic processes of the microorganism, including the processes that keep the microorganism alive.

The term, "effectiveness" as used herein refers to ability of a treatment, or a composition, or one or more pharmaceutically active ingredients to produce a desired biological effect in a subject. For example, the term "antibacterial effectiveness" of a composition or of an antibacterial agent refers to the ability of the composition or the antibacterial agent to prevent or treat bacterial infection in a subject.

The term "synergistic" or "synergy" as used herein refers to the interaction of two or more agents so that their combined effect is greater than their individual effects.

The term "antibacterial agent" as used herein refers to any substance, compound, a combination of substances, or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" or "beta-lactamase enzyme" as used herein refers to any enzyme or protein or any other substance that breaks down a beta-lactam ring. The term "beta-lactamase" includes enzymes that are produced by bacteria and have the ability to hydrolyse the beta-lactam ring in a beta-lactam compound, either partially or completely.

The term "extended spectrum beta-lactamase" (ESBL) as used herein includes those beta-lactamase enzymes, which are capable of conferring bacterial resistance to various beta-lactam antibacterial agents such as penicillins, cephalosporins, aztreonam and the like.

The term "beta-lactamase inhibitor" as used herein refers to a compound capable of inhibiting activity of one or more beta-lactamase enzymes, either partially or completely.

The term "colony forming units" or "CFU" as used herein refers to an estimate of number of viable bacterial cells per ml of the sample. Typically, a "colony of bacteria" refers to a mass of individual bacteria growing together.

The term "pharmaceutically inert ingredient" or "carrier" or "excipient" refers to and includes compounds or materials used to facilitate administration of a compound, for example, to increase the solubility of the compound. Typical, non-limiting examples of solid carriers include starch, lactose, dicalcium phosphate, sucrose, and kaolin. Typical, non-limiting examples of liquid carriers include sterile water, saline, buffers, non-ionic surfactants, and edible oils. In addition, various adjuvants commonly used in the art may also be included. These and other such compounds are described in literature, e.g., in the Merck Index (Merck & Company, Rahway, N.J.). Considerations for inclusion of various components in pharmaceutical compositions are described, e.g., in Gilman et al. (Goodman and Gilman's: The Pharmacological Basis of Therapeutics, 8th Ed., Pergamon Press., 1990), which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" include humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salts, pro-drugs, metabolites, esters, ethers, hydrates, polymorphs, solvates, complexes, and adducts) which, upon administration to a subject, are capable of providing (directly or indirectly) the antibacterial agent.

The term "pharmaceutically acceptable salt" as used herein refers to one or more salts of a given compound which possesses desired pharmacological activity of the free compound and which is neither biologically nor otherwise undesirable. In general, the term "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutically acceptable salts in details.

The term "stereoisomer" as used herein refers to and includes isomeric molecules that have the same molecular formula but differ in positioning of atoms and/or functional groups in the space. Stereoisomers may further be classified as enantiomers (where different isomers are mirror-images of each other) and diastereomers (where different isomers are not mirror-images of each other). Diastereomers include isomers such as conformers, meso compounds, cis-trans (E-Z) isomers, and non-enantiomeric optical isomers.

A person of skills in the art would appreciate that various compounds described herein (including, for example a compound of Formula (I), imipenem and cilastatin) can exist and are often used as their pharmaceutically acceptable derivatives (such as salts, pro-drugs, metabolites, esters, ethers, hydrates, polymorphs, solvates, complexes, and adducts).

In one general aspect, there are provided pharmaceutical compositions comprising: (a) imipenem or a pharmaceutically acceptable derivative thereof, and (b) a compound of Formula (I) or a stereoisomer or a pharmaceutically acceptable derivative thereof:

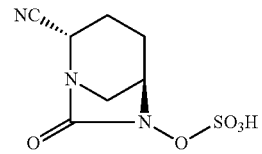

Formula (I)

Compound of Formula (I), according to the invention can be used in various forms including as such, a stereoisomer or a pharmaceutically acceptable derivative thereof. A compound of Formula (I) (CAS Registry Number: 1427462-70-1) may also be known chemically by different names including the following: (a) "trans-7-oxo-6-(sulphooxy)-1,6-diazabicyclo[3.2.1]octane-2-carbonitrile"; (b) "(2S,5R)-7-oxo-6-(sulphooxy)-1,6-diazabicyclo[3.2.1]octane-2-carbonitrile"; or (c) "Sulphuric acid, mono[(1R,2S,5R)-2-cyano-7-oxo-1,6-diazabicyclo[3.2.1]oct-6-yl] ester". A reference to "a compound of Formula (I)" is intended to include compounds chemically known as: (a) "trans-7-oxo-6-(sulphooxy)-1,6-diazabicyclo[3.2.1]octane-2-carbonitrile"; (b) "(2S,5R)-7-oxo-6-(sulphooxy)-1,6-diazabicyclo[3.2.1]octane-2-carbonitrile"; or (c) "Sulphuric acid, mono[(1R,2S,5R)-2-cyano-7-oxo-1,6-diazabicyclo[3.2.1]oct-6-yl] ester".

Compound of Formula (I) may also be used in the form of its stereoisomer or a pharmaceutically acceptable derivative thereof. Typical, non-limiting examples of suitable pharmaceutically acceptable derivatives of a compound of Formula (I) include its sodium salt (also known as "sodium salt of sulphuric acid, mono[(1R,2S,5R)-2-cyano-7-oxo-1,6-diazabicyclo[3.2.1]oct-6-yl] ester" or "sulphuric acid, mono[(1R,2S,5R)-2-cyano-7-oxo-1,6-diazabicyclo[3.2.1]oct-6-yl] ester, sodium salt (1:1); CAS Registry Number: 1427462-59-6"); potassium salt (also known as "potassium salt of sulphuric acid, mono[(1R,2S,5R)-2-cyano-7-oxo-1,6-diazabicyclo[3.2.1]oct-6-yl] ester" or "sulphuric acid, mono[(1R,2S,5R)-2-cyano-7-oxo-1,6-diazabicyclo[3.2.1]oct-6-yl] ester, potassium salt (1:1); CAS Registry Number: 1427462-60-9"); and other salts such as "1-Butanaminium, N,N,N-tributyl-, (1R,2S,5R)-2-cyano-7-oxo-1,6-diazabicyclo[3.2.1]oct-6-yl sulphate (1:1); CAS Registry Number: 1427462-72-3".

In another general aspect, there are provided pharmaceutical compositions comprising: (a) imipenem or a pharmaceutically acceptable derivative thereof, and (b) a compound of Formula (I) or a stereoisomer or a pharmaceutically acceptable derivative thereof; wherein a compound of Formula (I) or a stereoisomer or a pharmaceutically acceptable derivative thereof is present in the composition in an amount from about 0.25 gram to about 4 gram per gram of imipenem or a pharmaceutically acceptable derivative thereof.

Both, imipenem and a compound of Formula (I) may be present in the composition in their free forms or in the form of their pharmaceutically acceptable derivatives (such as salts, pro-drugs, metabolites, esters, ethers, hydrates, polymorphs, solvates, complexes, or adducts).

Individual amounts of a compound of Formula (I) or a stereoisomer or a pharmaceutically acceptable derivative thereof, and imipenem or pharmaceutically acceptable derivative thereof in the composition may vary depending on clinical requirements. In some embodiments, a compound of Formula (I) or a stereoisomer or a pharmaceutically acceptable derivative thereof in the composition is present in an amount from about 0.01 gram to about 10 gram. In some other embodiments, imipenem or a pharmaceutically acceptable derivative thereof in the composition is present in an amount from about 0.01 gram to about 10 gram.

In some embodiments, the pharmaceutical composition according to the invention comprises about 0.25 gram of a compound of Formula (I) or a stereoisomer or a pharmaceutically acceptable derivative thereof, and about 0.5 gram of imipenem or a pharmaceutically acceptable derivative thereof.

In some other embodiments, the pharmaceutical composition according to the invention comprises about 0.5 gram of a compound of Formula (I) or a stereoisomer or a pharmaceutically acceptable derivative thereof, and about 0.5 gram of imipenem or a pharmaceutically acceptable derivative thereof.

In some embodiments, the pharmaceutical composition according to the invention comprises about 1 gram of a compound of Formula (I) or a stereoisomer or a pharmaceutically acceptable derivative thereof, and about 0.5 gram of imipenem or a pharmaceutically acceptable derivative thereof.

In some embodiments, the pharmaceutical composition according to the invention comprises about 2 gram of a compound of Formula (I) or a stereoisomer or a pharmaceutically acceptable derivative thereof, and about 0.5 gram of imipenem or a pharmaceutically acceptable derivative thereof.

In some other embodiments, the pharmaceutical composition according to the invention comprises about 0.25 gram of a compound of Formula (I) or a stereoisomer or a pharmaceutically acceptable derivative thereof, and about 1 gram of imipenem or a pharmaceutically acceptable derivative thereof.

In some embodiments, the pharmaceutical composition according to the invention comprises about 0.5 gram of a compound of Formula (I) or a stereoisomer or a pharmaceutically acceptable derivative thereof, and about 1 gram of imipenem or a pharmaceutically acceptable derivative thereof.

In some embodiments, the pharmaceutical composition according to the invention comprises about 1 gram of a compound of Formula (I) or a stereoisomer or a pharmaceutically acceptable derivative thereof, and about 1 gram of imipenem or a pharmaceutically acceptable derivative thereof.

In some embodiments, the pharmaceutical composition according to the invention comprises about 2 gram of a compound of Formula (I) or a stereoisomer or a pharmaceutically acceptable derivative thereof, and about 1 gram of imipenem or a pharmaceutically acceptable derivative thereof.

In some embodiments, the pharmaceutical composition according to the invention comprises about 4 gram of a compound of Formula (I) or a stereoisomer or a pharmaceutically acceptable derivative thereof, and about 1 gram of imipenem or a pharmaceutically acceptable derivative thereof.

In some embodiments, the pharmaceutical composition according to the invention comprises about 2 gram of a compound of Formula (I) or a stereoisomer or a pharmaceutically acceptable derivative thereof, and about 2 gram of imipenem or a pharmaceutically acceptable derivative thereof.

In some other embodiments, the pharmaceutical composition according to the invention comprises about 1 gram of a compound of Formula (I) or a stereoisomer or a pharmaceutically acceptable derivative thereof, and about 2 gram of imipenem or a pharmaceutically acceptable derivative thereof.

The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatine, sucrose, magnesium carbonate, wetting agents, emulsifying agents, solubilizing agents, buffering agents, lubricants, preservatives, stabilizing agents, binding agents and the like.

The pharmaceutical compositions or the active ingredients according to the present invention may be formulated into a variety of dosage forms, such as solid, semi-solid, liquid and aerosol dosage forms. Typical, non-limiting examples of some dosage forms include tablets, capsules, powders, solutions, suspensions, suppositories, aerosols, granules, emulsions, syrups, elixirs and the like.

In some embodiments, pharmaceutical compositions according to the invention are in the form of a powder or a solution. In some other embodiments, pharmaceutical compositions according to the invention are present in the form of a powder or a solution that can be reconstituted by addition of a compatible reconstitution diluent prior to administration. In some other embodiments, pharmaceutical compositions according to the invention are in the form of a frozen composition that can be diluted with a compatible reconstitution diluent prior to administration. Typical, non-limiting example of suitable compatible reconstitution diluent includes water.

In some other embodiments, pharmaceutical compositions according to the invention are present in the form ready to use for parenteral administration.

The compositions according to the invention can be formulated into various dosage forms wherein the active ingredients and/or excipients may be present either together (e.g. as an admixture) or as separate components. When the various ingredients in the composition are formulated as a mixture, such compositions can be delivered by administering such a mixture to a subject using any suitable route of administration. Alternatively, pharmaceutical compositions according to the invention may also be formulated into a dosage form wherein one or more ingredients (such as active or inactive ingredients) are present as separate components. The composition or dosage form wherein the ingredients do not come as a mixture, but come as separate components, such composition/dosage form may be administered in several ways. In one possible way, the ingredients may be mixed in the desired proportions and the mixture is reconstituted in suitable reconstitution diluent and is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

In some embodiments, pharmaceutical compositions according to the invention are formulated into a dosage form such that a compound of Formula (I) or a stereoisomer or a pharmaceutically acceptable derivative thereof, and imipenem or a pharmaceutically acceptable derivative thereof, are present in the composition as admixture or as a separate components. In some other embodiments, pharmaceutical compositions according to the invention are formulated into a dosage form such that a compound of Formula (I) or a stereoisomer or a pharmaceutically acceptable derivative thereof, and imipenem or a pharmaceutically acceptable derivative thereof, are present in the composition as separate components.

In one general aspect, pharmaceutical compositions according to the invention are used in treatment or prevention of a bacterial infection.

In another general aspect, there are provided methods for treating or preventing a bacterial infection in a subject, said method comprising administering to said subject effective amount of a pharmaceutical composition according to the invention. In case of dosage forms wherein a compound of Formula (I) or a stereoisomer or a pharmaceutically acceptable derivative thereof, and imipenem or a pharmaceutically acceptable derivative thereof, are present in the composition as separate components; a compound of Formula (I) or a stereoisomer or a pharmaceutically acceptable derivative thereof may be administered before, after or simultaneously with the administration of imipenem or a pharmaceutically acceptable derivative thereof.

In yet another general aspect, there are provided methods for treating or preventing bacterial infections in a subject, said methods comprising administering to said subject an effective amount of: (a) imipenem or a pharmaceutically acceptable derivative thereof, and (b) a compound of Formula (I) or a stereoisomer or a pharmaceutically acceptable derivative thereof:

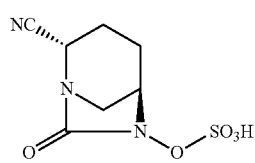

Formula (I)

In another general aspect, there are provided methods for treating or preventing bacterial infections in a subject, said methods comprising administering to said subject an effective amount of: (a) imipenem or a pharmaceutically acceptable derivative thereof, and (b) a compound of Formula (I) or a stereoisomer or a pharmaceutically acceptable derivative thereof; wherein amount of a compound of Formula (I) or a stereoisomer or a pharmaceutically acceptable derivative thereof administered is from about 0.25 gram to about 4 gram per gram of imipenem or a pharmaceutically acceptable derivative thereof.

In some embodiments, there is provided a method for treating or preventing a bacterial infection in a subject, said method comprising administering to said subject: (a) imipenem or a pharmaceutically acceptable derivative thereof, and (b) a compound of Formula (I) or a stereoisomer or a pharmaceutically acceptable derivative thereof, in any of the following amounts:

(i) about 0.25 gram of a compound of Formula (I) or a stereoisomer or a pharmaceutically acceptable derivative thereof, and about 0.5 gram of imipenem or a pharmaceutically acceptable derivative thereof;

(ii) about 0.5 gram of a compound of Formula (I) or a stereoisomer or a pharmaceutically acceptable derivative thereof, and about 0.5 gram of imipenem or a pharmaceutically acceptable derivative thereof;

(iii) about 1 gram of a compound of Formula (I) or a stereoisomer or a pharmaceutically acceptable derivative thereof, and about 0.5 gram of imipenem or a pharmaceutically acceptable derivative thereof;

(iv) about 2 gram of a compound of Formula (I) or a stereoisomer or a pharmaceutically acceptable derivative thereof, and about 0.5 gram of imipenem or a pharmaceutically acceptable derivative thereof;

(v) about 0.25 gram of a compound of Formula (I) or a stereoisomer or a pharmaceutically acceptable derivative thereof, and about 1 gram of imipenem or a pharmaceutically acceptable derivative thereof;

(vi) about 0.5 gram of a compound of Formula (I) or a stereoisomer or a pharmaceutically acceptable derivative thereof, and about 1 gram of imipenem or a pharmaceutically acceptable derivative thereof;

(vii) about 1 gram of a compound of Formula (I) or a stereoisomer or a pharmaceutically acceptable derivative thereof, and about 1 gram of imipenem or a pharmaceutically acceptable derivative thereof;

(viii) about 2 gram of a compound of Formula (I) or a stereoisomer or a pharmaceutically acceptable derivative thereof, and about 1 gram of imipenem or a pharmaceutically acceptable derivative thereof;

(ix) about 4 gram of a compound of Formula (I) or a stereoisomer or a pharmaceutically acceptable derivative thereof, and about 1 gram of imipenem or a pharmaceutically acceptable derivative thereof;

(x) about 2 gram of a compound of Formula (I) or a stereoisomer or a pharmaceutically acceptable derivative thereof, and about 2 gram of imipenem or a pharmaceutically acceptable derivative thereof; or (xi) about 1 gram of a compound of Formula (I) or a stereoisomer or a pharmaceutically acceptable derivative thereof, and about 2 gram of imipenem or a pharmaceutically acceptable derivative thereof.

In some embodiments, in the methods according to the invention, a compound of Formula (I) or a stereoisomer or a pharmaceutically acceptable derivative thereof is administered in an amount from about 0.01 gram to about 10 gram. In some other embodiments, in the methods according to the invention, imipenem or a pharmaceutically acceptable derivative thereof is administered in an amount from about 0.01 gram to about 10 gram.

In some embodiments, in the methods according to the invention, a compound of Formula (I) or a stereoisomer or a pharmaceutically acceptable derivative thereof is administered before, after or simultaneously with the administration of imipenem or a pharmaceutically acceptable derivative thereof.

In the methods according to the invention, the pharmaceutical composition and/or other pharmaceutically active ingredients disclosed herein may be administered by any appropriate method, which serves to deliver the composition, or its constituents, or the active ingredients to the desired site. The method of administration can vary depending on various factors, such as for example, the components of the pharmaceutical composition and the nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, the compositions or one or more active ingredients according to the invention are administered parenterally.

In some embodiments, in the compositions and methods according to the invention, a compound of Formula (I) is "(2S,5R)-7-oxo-6-(sulphooxy)-1,6-diazabicyclo[3.2.1]octane-2-carbonitrile". In some other embodiments, in the compositions and methods according to the invention, a compound of Formula (I) is: "sulphuric acid, mono[(1R,2S,5R)-2-cyano-7-oxo-1,6-diazabicyclo[3.2.1]oct-6-yl] ester". In some embodiments, in compositions and methods according to the invention, a compound of Formula (I) is present as a sodium or potassium salt of "sulphuric acid, mono[(1R,2S,5R)-2-cyano-7-oxo-1,6-diazabicyclo[3.2.1]oct-6-yl] ester".

In general, imipenem is known to be susceptible to degradation by a renal enzyme known as dehydropeptidase (DHP), which may reduce overall availability of imipenem and reduce the efficacy of the treatment. One way to minimize degradation of imipenem by dehydropeptidase is to co-administer imipenem with a suitable dehydropeptidase inhibitor (DHP inhibitor). Typical, non-limiting example of a suitable dehydropeptidase inhibitor includes cilastatin or a pharmaceutically acceptable derivative thereof. In some embodiments, the pharmaceutical compositions and methods according to invention comprise use of a suitable dehydropeptidase inhibitor. When used in compositions, the dehydropeptidase inhibitor may be present in the composition in admixture with one or more ingredients or as a separate component. When used in methods according to the invention, the dehydropeptidase inhibitor may be administered together with the composition or given separate from the composition (or its components).

In some embodiments, pharmaceutical compositions according to the invention further comprise a dehydropeptidase inhibitor. In some other embodiments, pharmaceutical compositions according to the invention comprise a dehydropeptidase inhibitor, which is cilastatin or a pharmaceutically acceptable derivative thereof. In some embodiments, the methods according to the invention further comprise administration of a dehydropeptidase inhibitor. In some other embodiments, the methods according to the invention comprise administration of a dehydropeptidase inhibitor, which is cilastatin or a pharmaceutically acceptable derivative thereof.

The amount of a dehydropeptidase inhibitor that can be used in the compositions or methods according to the invention depends on the therapeutic effect desired. In some embodiments, the dehydropeptidase inhibitor is used in an amount which is about 0.1 to about 10 gram per gram of imipenem. In some other embodiments, the weight ratio of dehydropeptidase inhibitor to imipenem used in the pharmaceutical compositions and methods according to the invention is about 1:1.

In some embodiments, there is provided a method for increasing antibacterial effectiveness of imipenem or a pharmaceutically acceptable derivative thereof in a subject, said method comprising co-administering imipenem or a pharmaceutically acceptable derivative thereof, with a compound of Formula (I) or a stereoisomer or a pharmaceutically acceptable derivative thereof. In some other embodiments, there is provided a method for increasing antibacterial effectiveness of imipenem or a pharmaceutically acceptable derivative thereof in a subject, said method comprising co-administering imipenem or a pharmaceutically acceptable derivative thereof, with a compound of Formula (I) or a stereoisomer or a pharmaceutically acceptable derivative thereof, wherein the amount of a compound of Formula (I) or a stereoisomer or a pharmaceutically acceptable derivative thereof is from about 0.25 gram to about 4 gram per gram of imipenem or a pharmaceutically acceptable derivative thereof.

A wide variety of bacterial infections can be treated or prevented using compositions and methods according to the invention. Typical, non-limiting examples of bacterial infections that can be treated or prevented using methods and/or pharmaceutical compositions according to the invention include *E. coli* infections, *Yersinia pestis* (pneumonic plague), staphylococcal infection, mycobacteria infection, bacterial pneumonia, *Shigella* dysentery, *Serratia* infections, *Candida* infections, *Cryptococcal* infection, anthrax, tuberculosis or infections caused by *Pseudomonas aeruginosa*, *Acinetobacter baumannii* or methicillin resistant *Staphylococcus aurues* (MRSA) etc.

The pharmaceutical compositions and methods according to the invention are useful in treatment or prevention of several infections, including for example, skin and soft tissue infections, febrile neutropenia, urinary tract infection, intraabdominal infections, respiratory tract infections, pneumonia (nosocomial), bacteremia meningitis, surgical infections and the like.

In some embodiments, pharmaceutical compositions and methods according to the invention are used in treatment or prevention of infections caused by resistant bacteria. In some other embodiments, the compositions and methods according to the invention are used in treatment or prevention of infections caused by bacteria producing one or more beta-lactamase enzymes.

In general, the pharmaceutical compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, Escherichia coli, Pseudomonas aeruginosa, Staphylococcus aureus, Enterobacter, Klebsiella, Citrobacter* and a like.

EXAMPLES

The following examples illustrate embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical embodiments of the invention.

The antibacterial activity of compositions according to the invention against various bacterial strains was investigated. In a typical study, freshly grown cultures were diluted to required cell density (initial starting inoculum) in Mueller Hinton broth medium (BD, USA). The antibacterial agents, either alone or in combination, at required concentrations were added into the medium containing the desired initial starting inoculum. The samples were incubated under shaking condition (120 rpm) at 37° C. Enumeration of viable bacterial count was undertaken, every 2 hours, by diluting in normal saline and plating on to the Tryptic Soya Agar plates (BD, USA). The plates were incubated for 24 hours to arrive at the viable bacterial count. The antibacterial activity is expressed in terms of Colony Forming Units (CFU). The decrease of 1 Log CFU/ml, after administration of combination of present invention, in comparison to initial bacterial count corresponds to 90% killing of bacteria. Similarly, 2 Log CFU/ml reductions corresponds to 99% killing of bacteria and 3 Log CFU/ml reductions is equal to 99.9% killing of bacteria.

Formula (I) (4 mcg/ml) exhibited the decrease in bacterial counts in the initial hours (up to 8 hours) but failed to exhibit the antibacterial activity at 24 hours. Additionally, initial rate of killing exhibited by combinations of meropenem/sodium salt of a compound of Formula (I) and dorepenem/sodium salt of a compound of Formula (I) was lower than that shown by combination of imipenem and a sodium salt of a compound of Formula (I). The data reveals that combinations comprising meropenem and dorepenem exhibited lesser antibacterial activity with much shorter duration of action in comparison to the combinations comprising imipenem. Thus, the combination of imipenem and sodium salt of a compound of Formula (I) exhibited unexpected and enhanced antibacterial activity for longer period of times.

TABLE 1

Antibacterial activity of a combination comprising imipenem and sodium salt of compound of Formula (I) against *A. baumannii* S 226 strain producing CHDL Oxacillinases (OXA 51, OXA-23)

| | | Bacterial count ($Log_{10}$ CFU/ml) | | | | |
|---|---|---|---|---|---|---|
| Sr. | Active ingredient | 2 hours | 4 hours | 6 hours | 8 hours | 24 hours |
| 1. | Control (No active ingredient) | 8.09 | 7.93 | 8.7 | 8.49 | 8.00 |
| 2. | Imipenem (8 mcg/ml) | 7.46 | 8.26 | 8.43 | 8.52 | 8.74 |
| 3. | Meropenem (8 mcg/ml) | 8.00 | 8.34 | 8.45 | 8.65 | 8.70 |
| 4. | Doripenem (8 mcg/ml) | 7.95 | 8.08 | 8.12 | 8.50 | 8.30 |
| 5 | Sodium salt of a compound of Formula (I) (4 mcg/ml) | 7.93 | 7.95 | 8.20 | 8.50 | 8.60 |
| 6. | Imipenem (4 mcg/ml) + sodium salt of a compound of Formula (I) (4 mcg/ml) | 5.08 | 3.81 | 4.48 | 5.74 | 7.78 |
| 7. | Imipenem (8 mcg/ml) + sodium salt of a compound of Formula (I) (4 mcg/ml) | 4.23 | 3.30 | 3.00 | 2.77 | 1.48 |
| 8. | Meropenem (4 mcg/ml) + sodium salt of a compound of Formula (I) (4 mcg/ml) | 6.52 | 4.60 | 3.95 | 4.95 | 7.98 |
| 9. | Meropenem (8 mcg/ml) + sodium salt of a compound of Formula (I) (4 mcg/ml) | 5.32 | 3.78 | 3.60 | 3.15 | 8.00 |
| 10. | Doripenem (4 mcg/ml) + sodium salt of a compound of Formula (I) (4 mcg/ml) | 6.75 | 5.45 | 4.48 | 5.26 | 8.38 |
| 11. | Doripenem (8 mcg/ml) + sodium salt of a compound of Formula (I) (4 mcg/ml) | 6.15 | 4.08 | 4.15 | 5.18 | 8.00 |

Initial bacterial count (at 0 hours) was 6.62 log CFU/ml

Example 1

The results on antibacterial activity of the combination according to invention are given in Table 1. The combination according to invention was tested against highly resistant *A. baumannii* S 226 strain producing Carbapenem hydrolyzing (CHDL) Oxacillinases [OXA-51, OXA-23]. The assay without any antibacterial agent was taken as control. As can be seen from the data in Table 1, imipenem (at 8 mcg/ml), meropenem (at 8 mcg/ml), doripenem (at 8 mcg/ml) and a sodium salt of a compound of Formula (I) (at 4 mcg/ml) when used alone failed to decrease the bacterial count of *A. baumannii* throughout the duration of the study. However, surprisingly it has been observed that the combination of imipenem and a sodium salt of a compound of Formula exhibited synergistic killing of *A. baumannii* for extended period of times.

The data also reveals that combination of imipenem (at 8 mcg/ml) and a sodium salt of a compound of Formula (I) (at 4 mcg/ml) reduced bacterial count to 1.48 Log CFU/ml at end of 24 hours. Also, it can be seen that both: (a) a combination of meropenem (at both 4 mcg/ml and 8 mcg/ml) and a sodium salt of a compound of Formula (I) (4 mcg/ml) and (b) a combination of doripenem (at both 4 mcg/ml and 8 mcg/ml) and a sodium salt of a compound of

The invention claimed is:

1. A pharmaceutical composition comprising: (a) imipenem or a pharmaceutically acceptable salt thereof, and (b) a compound of Formula (I):

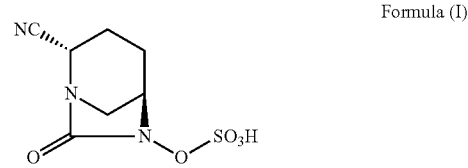 [SMILES: N#C[C@@H]1CC[C@@H]2CN1C(=O)N2OS(=O)(=O)O]

Formula (I)

or a stereoisomer or a pharmaceutically acceptable salt thereof.

2. The pharmaceutical composition according to claim 1, wherein the compound of Formula (I) or stereoisomer or pharmaceutically acceptable salt thereof is present in the composition in an amount from about 0.01 grams to about 10 grams.

3. The pharmaceutical composition according to claim 1, wherein the imipenem or pharmaceutically acceptable salt thereof is present in the composition in an amount from about 0.01 grams to about 10 grams.

4. The pharmaceutical composition according to claim 1, comprising: (a) the imipenem or pharmaceutically acceptable salt thereof, and (b) the compound of Formula (I) or stereoisomer or pharmaceutically acceptable salt thereof, in any of the following amounts:
(i) about 0.25 grams of the compound of Formula (I) or stereoisomer or pharmaceutically acceptable salt thereof, and about 0.5 grams of the imipenem or pharmaceutically acceptable salt thereof;
(ii) about 0.5 grams of the compound of Formula (I) or stereoisomer or pharmaceutically acceptable salt thereof, and about 0.5 grams of the imipenem or pharmaceutically acceptable salt thereof;
(iii) about 1 gram of the compound of Formula (I) or stereoisomer or pharmaceutically acceptable salt thereof, and about 0.5 grams of the imipenem or pharmaceutically acceptable salt thereof;
(iv) about 2 grams of the compound of Formula (I) or stereoisomer or pharmaceutically acceptable salt thereof, and about 0.5 grams of the imipenem or pharmaceutically acceptable salt thereof;
(v) about 0.25 grams of the compound of Formula (I) or stereoisomer or pharmaceutically acceptable salt thereof, and about 1 gram of the imipenem or pharmaceutically acceptable salt thereof;
(vi) about 0.5 grams of the compound of Formula (I) or stereoisomer or pharmaceutically acceptable derivative salt, and about 1 gram of the imipenem or pharmaceutically acceptable salt thereof;
(vii) about 1 gram of the compound of Formula (I) or stereoisomer or pharmaceutically acceptable salt thereof, and about 1 gram of the imipenem or pharmaceutically acceptable salt thereof;
(viii) about 2 grams of the compound of Formula (I) or stereoisomer or pharmaceutically acceptable salt thereof, and about 1 gram of the imipenem or pharmaceutically acceptable salt thereof;
(ix) about 4 grams of the compound of Formula (I) or stereoisomer or pharmaceutically acceptable salt thereof, and about 1 gram of the imipenem or pharmaceutically acceptable salt thereof;
(x) about 2 grams of the compound of Formula (I) or stereoisomer or pharmaceutically acceptable salt thereof, and about 2 grams of the imipenem or pharmaceutically acceptable salt thereof; or
(xi) about 1 gram of the compound of Formula (I) or stereoisomer or pharmaceutically acceptable salt thereof, and about 2 grams of the imipenem or pharmaceutically acceptable salt thereof.

5. The pharmaceutical composition according to claim 1, wherein the compound of Formula (I) is: "(2S,5R)-7-oxo-6-(sulphooxy)-1,6-diazabicyclo[3.2.1]octane-2-carbonitrile" or "sulphuric acid, mono[(1R,2S,5R)-2-cyano-7-oxo-1,6-diazabicyclo[3.2.1]oct-6-yl] ester" or "sodium or potassium salt of "sulphuric acid, mono[(1R,2S,5R)-2-cyano-7-oxo-1,6-diazabicyclo[3.2.1]oct-6-yl] ester".

6. The pharmaceutical composition according to claim 1; wherein said pharmaceutical composition further comprising a dehydropeptidase inhibitor.

7. The pharmaceutical composition according to claim 1, wherein the composition is formulated into a dosage form such that the compound of Formula (I) or stereoisomer or pharmaceutically acceptable salt thereof, and the imipenem or pharmaceutically acceptable salt thereof are present in the composition as admixture or as separate components.

8. The pharmaceutical composition according to claim 1, wherein the composition is in the form of a powder or a solution.

9. The pharmaceutical composition according to claim 8, wherein the composition is in the form of a powder or a solution that can be reconstituted by addition of a compatible reconstitution diluent for use in parenteral administration.

10. A pharmaceutical composition of claim 1, wherein the compound of Formula (I); or a pharmaceutically acceptable salt, or stereoisomer thereof is present in the composition in an amount from about 0.25 grams to about 4 grams per gram of the imipenem or pharmaceutically acceptable salt thereof.

11. The pharmaceutical composition according to claim 6, wherein the dehydropeptidase inhibitor is cilastatin or pharmaceutically acceptable derivative thereof.

12. A method for treating a bacterial infection comprising administering to subject in need thereof the pharmaceutical composition according to claim 1.

13. A method for treating a bacterial infection, comprising administering to a subject in need thereof an effective amount of: (a) imipenem or a pharmaceutically acceptable salt thereof, and (b) a compound of Formula (I):

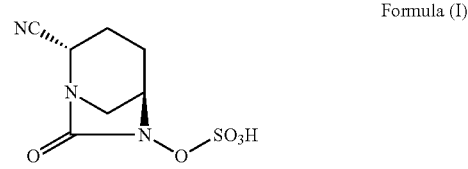 [SMILES: N#C[C@@H]1CC[C@@H]2CN1C(=O)N2OS(=O)(=O)O]

Formula (I)

or a stereoisomer or a pharmaceutically acceptable salt thereof.

14. The method according to claim 13, wherein the compound of Formula (I) or stereoisomer or pharmaceutically acceptable salt thereof is administered in an amount from about 0.01 grams to about 10 grams.

15. The method according to claim 13, wherein the imipenem or pharmaceutically acceptable salt thereof is administered in an amount from about 0.01 grams to about 10 grams.

16. The method according to claim 13, wherein the imipenem or pharmaceutically acceptable salt thereof, and the compound of Formula (I) or stereoisomer or pharmaceutically acceptable salt thereof are administered in any of the following amounts:
(i) about 0.25 grams of the compound of Formula (I) or stereoisomer or pharmaceutically acceptable salt thereof, and about 0.5 grams of the imipenem or pharmaceutically acceptable salt thereof;
(ii) about 0.5 grams of the compound of Formula (I) or stereoisomer or pharmaceutically acceptable salt thereof, and about 0.5 grams of imipenem or pharmaceutically acceptable salt thereof;
(iii) about 1 gram of the compound of Formula (I) or stereoisomer or pharmaceutically acceptable salt thereof, and about 0.5 grams of the imipenem or pharmaceutically acceptable salt thereof;
(iv) about 2 grams of the compound of Formula (I) or stereoisomer or pharmaceutically acceptable salt thereof, and about 0.5 grams of the imipenem or pharmaceutically acceptable salt thereof;
(v) about 0.25 grams of the compound of Formula (I) or stereoisomer or pharmaceutically acceptable salt thereof, and about 1 gram of the imipenem or pharmaceutically acceptable salt thereof;
(vi) about 0.5 grams of the compound of Formula (I) or stereoisomer or pharmaceutically acceptable salt thereof, and about 1 gram of the imipenem or pharmaceutically acceptable salt thereof;

(vii) about 1 gram of the compound of Formula (I) or stereoisomer or pharmaceutically acceptable salt thereof, and about 1 gram of the imipenem or pharmaceutically acceptable salt thereof;

(viii) about 2 grams of the compound of Formula (I) or stereoisomer or pharmaceutically acceptable salt thereof, and about 1 gram of the imipenem or pharmaceutically acceptable salt thereof;

(ix) about 4 grams of the compound of Formula (I) or stereoisomer or pharmaceutically acceptable salt thereof, and about 1 gram of the imipenem or pharmaceutically acceptable salt thereof;

(x) about 2 grams of the compound of Formula (I) or stereoisomer or pharmaceutically acceptable salt thereof, and about 2 grams of the imipenem or pharmaceutically acceptable salt thereof; or (xi) about 1 gram of the compound of Formula (I) or stereoisomer or pharmaceutically acceptable salt thereof, and about 2 grams of the imipenem or pharmaceutically acceptable salt thereof.

17. The method according to claim 13, wherein the compound of Formula (I) or stereoisomer or pharmaceutically acceptable salt thereof is administered before imipenem or pharmaceutically acceptable salt thereof.

18. The method according to claims 13, further comprising an administration of a dehydropeptidase inhibitor.

19. The method according to claim 13, wherein the compound of Formula (I) or stereoisomer or pharmaceutically acceptable salt thereof is administered after the imipenem or pharmaceutically acceptable salt thereof.

20. The method according to claim 13, wherein the compound of Formula (I) or stereoisomer or pharmaceutically acceptable salt thereof is administered simultaneously with the imipenem or pharmaceutically acceptable salt thereof.

21. A method for increasing antibacterial effectiveness of imipenem or a pharmaceutically acceptable salt thereof comprising co-administering the imipenem or pharmaceutically acceptable salt thereof with a compound of Formula (I)

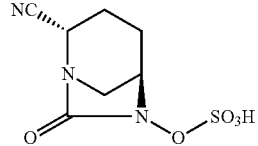

Formula (I)

or a stereoisomer or a pharmaceutically acceptable salt thereof.

22. The method according to claim 18, wherein the dehydropeptidase inhibitor is cilastatin.

23. The method according to claims 13; wherein the compound of Formula (I) or stereoisomer or pharmaceutically acceptable salt thereof is administered in an amount from about 0.25 grams to about 4 grams per gram of the imipenem or pharmaceutically acceptable salt thereof.

* * * * *